(12) United States Patent
Lin et al.

(10) Patent No.: US 8,076,592 B2
(45) Date of Patent: Dec. 13, 2011

(54) ELECTROMAGNETIC INTERFERENCE PREVENTING MODULE

(75) Inventors: Wen-Cheng Lin, Tao Yuan Shien (TW); Mao-Chen Hsiao, Taipei County (TW)

(73) Assignee: Quanta Computer Inc., Taoyuan Shien (TW)

( * ) Notice: Subject to any disclaimer, the term of this patent is extended or adjusted under 35 U.S.C. 154(b) by 322 days.

(21) Appl. No.: 12/585,332

(22) Filed: Sep. 11, 2009

(65) Prior Publication Data
US 2010/0326717 A1 Dec. 30, 2010

(30) Foreign Application Priority Data
Jun. 26, 2009 (TW) .............................. 98211612 U

(51) Int. Cl.
*H05K 9/00* (2006.01)
(52) U.S. Cl. .... 174/359; 174/387; 361/816; 439/607.13
(58) Field of Classification Search ................. 174/359, 174/387, 376; 361/816; 439/607.13
See application file for complete search history.

(56) References Cited

U.S. PATENT DOCUMENTS

| | | | | |
|---|---|---|---|---|
| 6,235,985 B1 * | 5/2001 | Dai | .............................. | 174/359 |
| 6,538,196 B1 * | 3/2003 | MacDonald et al. | ......... | 174/377 |
| 6,629,365 B2 * | 10/2003 | Denzene et al. | ................ | 29/841 |
| 6,858,793 B1 * | 2/2005 | Pels et al. | ...................... | 174/359 |
| 6,872,880 B2 * | 3/2005 | King et al. | .................... | 174/372 |
| 6,958,445 B1 * | 10/2005 | Boudreaux et al. | ........... | 174/359 |
| 6,972,963 B1 * | 12/2005 | Chou | ............................ | 361/760 |
| 6,979,773 B2 * | 12/2005 | Fursich | ........................ | 174/377 |
| 6,979,774 B2 * | 12/2005 | Abe et al. | ...................... | 174/377 |
| 6,995,314 B2 * | 2/2006 | Gottwald | ...................... | 174/359 |
| 7,202,422 B2 * | 4/2007 | Ogatsu | .......................... | 174/373 |
| 7,351,919 B1 * | 4/2008 | Knoke et al. | .................. | 174/382 |
| 2003/0024717 A1 * | 2/2003 | Knighten et al. | ............. | 174/350 |

* cited by examiner

*Primary Examiner* — Hung Ngo
(74) *Attorney, Agent, or Firm* — Rabin & Berdo, PC

(57) ABSTRACT

An electromagnetic interference preventing module is provided. The module includes a metal pad that is disposed on a circuit board. The metal pad includes a soldering portion and a grounding portion that are connected to each other. At least one fixing lug of a connector is soldered to the soldering portion. At least one protrusion of a grounding housing is in contact with the grounding portion, so as to electrically connect the connector with the grounding housing.

20 Claims, 5 Drawing Sheets

ELECTROMAGNETIC INTERFERENCE PREVENTING MODULE

RELATED APPLICATIONS

This application claims priority to Taiwan Application Serial Number 98211612, filed Jun. 26, 2009, which is herein incorporated by reference.

BACKGROUND

1. Field of Invention

The present invention relates to an electromagnetic interference preventing module.

2. Description of Related Art

Along with the rapid development of technology, various electronic devices have become a crucial part in our daily life. As the function of an electronic device evolves, the communication or data transferring between different electronic devices happens more frequently. One common connecting manner is to conduct data transferring through a cable.

For example, a notebook computer and a digital camera can be connected through a Universal Serial Bus (USB) cable. The two ends of the USB cable respectively connect to a connector of the notebook computer and a connector of the digital camera, so as to transfer images that are stored in the camera to the computer. In the notebook computer, the connector is commonly fixed onto a circuit board of the computer through its own lug. The housing of the notebook computer is provided with a corresponding opening to expose the connector.

When the notebook computer is applied an electromagnetic interference test or an electrostatic discharge test, or when a user touches the connector exposed from the opening, the interference or the electrostatic discharge may cause the connector to work improperly. In a worse case, the connector can be damaged.

In order to solve this problem, one common solution provided by manufacturers is to provide a spring finger, a conductive gasket, a foil or the like between the connector and the housing, through which the connector is electrically connected to the housing. However, the disposition of the additional element increases the inconvenience of assembling the notebook computer, and the cost rises as well.

SUMMARY

An electromagnetic interference preventing module is provided. The module includes a circuit board, a metal pad, a connector and a first grounding housing. The circuit board includes a first surface, an opposite second surface and at least one soldering hole. The soldering hole passes through the circuit board from the first surface to the second surface. The metal pad is disposed on the first surface and includes a soldering portion and a grounding portion. The soldering portion surrounds the soldering hole. The grounding portion connects with the soldering portion. The connector is disposed on the second surface and includes at least on fixing lug. The fixing lug penetrates through the soldering hole and is soldered to the soldering portion. The first grounding housing includes a first protrusion, which is in contact with the grounding portion on the first surface, to electrically connect with the connector.

According to one embodiment of the invention, the metal pad is further disposed on the second surface.

According to another embodiment of the invention, the fixing lug is soldered to the soldering portion on the first surface and the second surface.

According to yet another embodiment of the invention, the module further includes a second grounding housing. The second grounding housing includes a second protrusion that is in contact with the grounding portion on the second surface to electrically connect the connector with the second grounding housing.

According to a further embodiment of the invention, the first grounding housing includes a first metal layer for electrically connecting to an external ground. The first protrusion is covered by the first metal layer and is in contact with the grounding portion on the first surface through the first metal layer.

According to a further embodiment of the invention, the second grounding housing includes a second metal layer for electrically connecting to the external ground. The second protrusion is covered by the second metal layer and is in contact with the grounding portion on the second surface through the second metal layer.

In the foregoing electromagnetic interference preventing module of the embodiments of the invention, the connector is electrically connected to the grounding housing directly by way of having the protrusion of the grounding housing contact with the grounding portion of the metal pad. The electrostatic discharge and the electromagnetic interference applying to the connector are guided to the grounding housing, so that the operation quality of the connector is improved. Further, cost is saved due to the fact that there is no need to add a conductive element between the circuit board and the housing.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
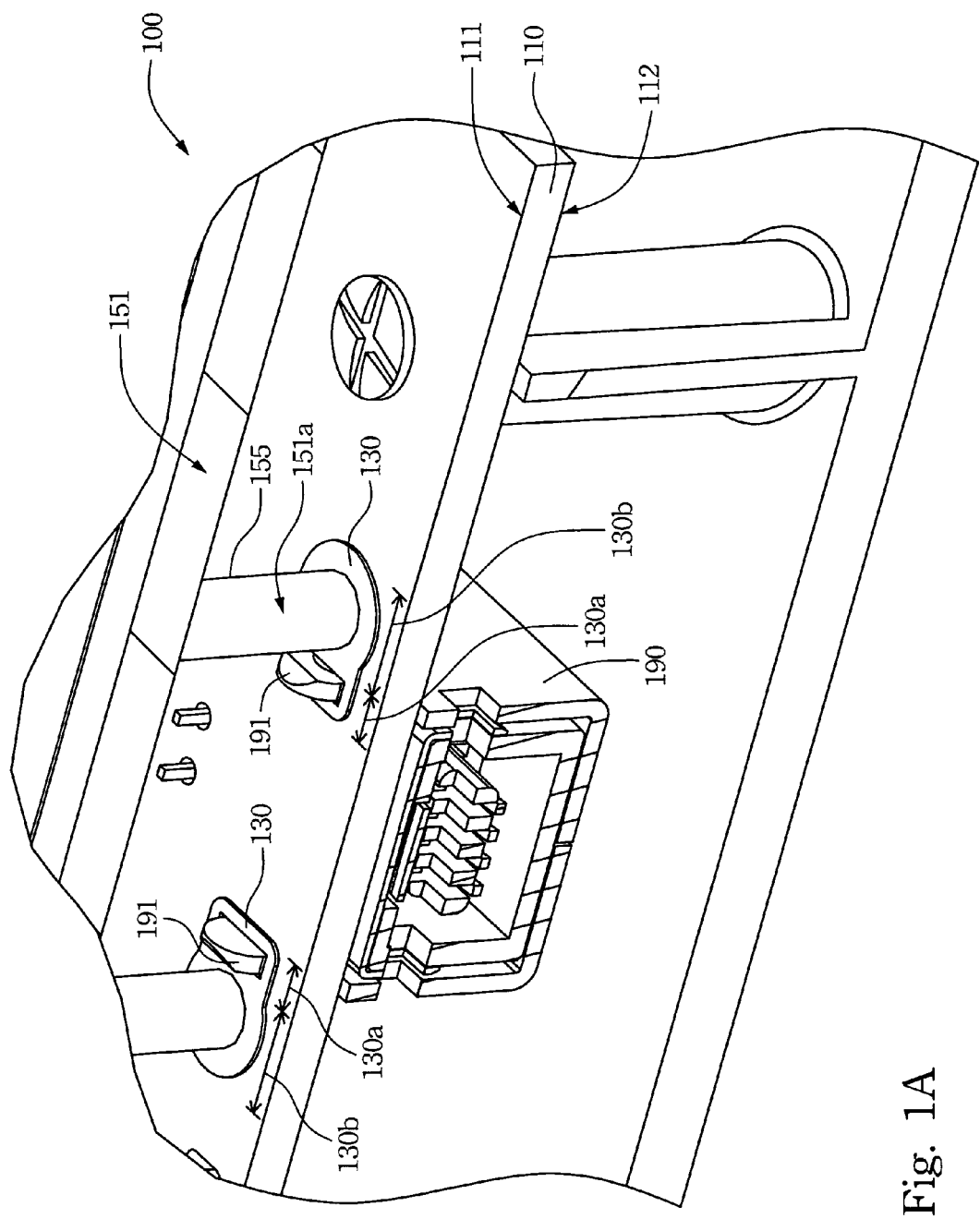
FIG. 1A is a perspective view of an electromagnetic interference preventing module of one embodiment of the invention.

Reference will now be made in detail to the present embodiments of the invention, examples of which are illustrated in the accompanying drawings. Wherever possible, the same reference numbers are used in the drawings and the description to refer to the same or like parts.

In the electromagnetic interference preventing module of the embodiments of the invention, the connector on the circuit board is electrically connected to the external ground through the grounding housing. Therefore the electromagnetic interference can be avoided, and the operation quality of the connector is improved.

Figure 1B:
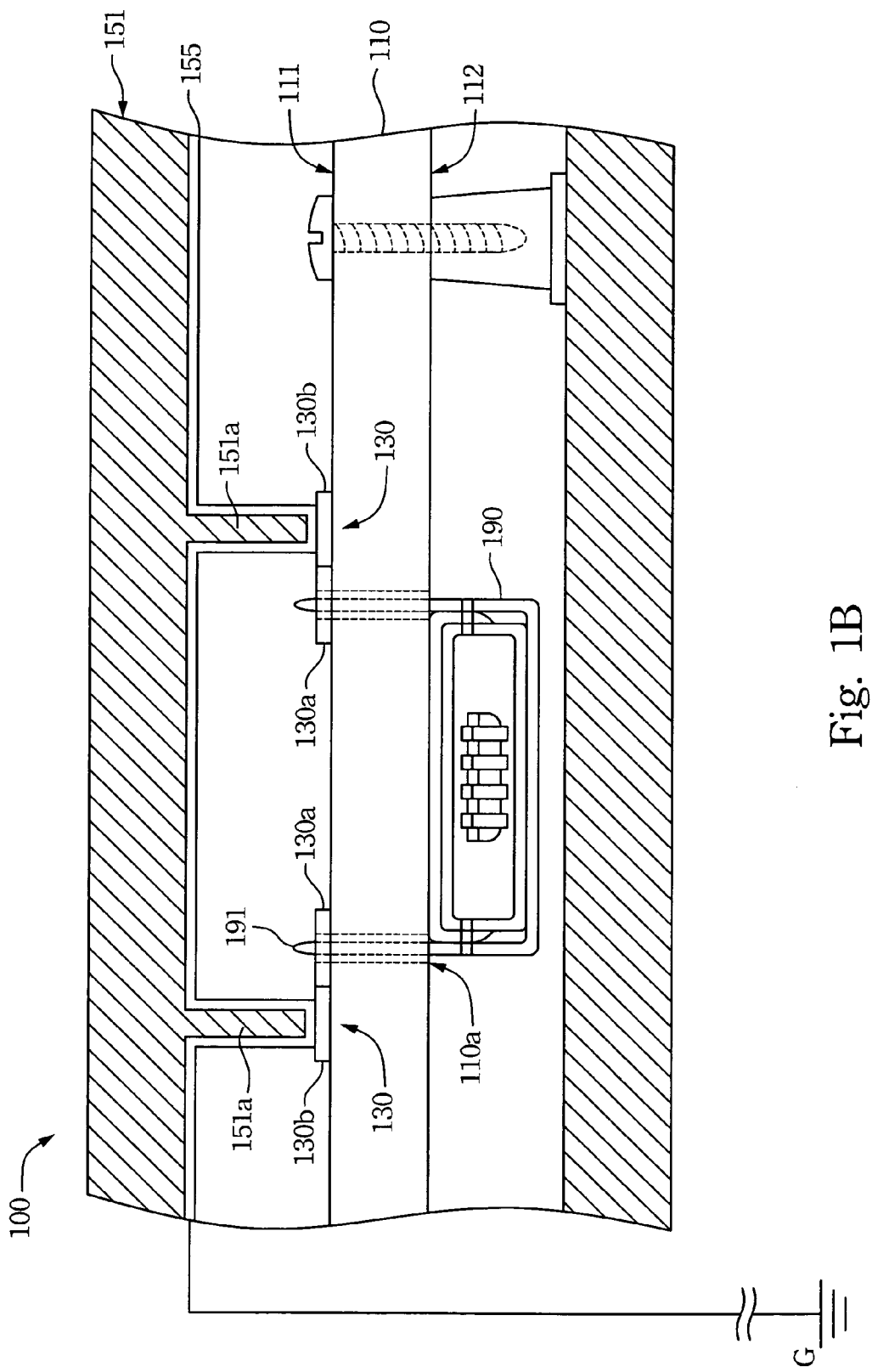
FIG. 1B is a side-view of the electromagnetic interference preventing module in FIG. 1A.

Please refer to FIG. 1A and FIG. 1B at the same time. FIG. 1A is a perspective view of an electromagnetic interference preventing module of one embodiment of the invention. FIG. 1B is a side-view of the electromagnetic interference preventing module in FIG. 1A. The electromagnetic interference preventing module 100 includes a circuit board 110, a metal pad 130 and a first grounding housing 151. The circuit board 110 includes at least one soldering hole 110a. In the electromagnetic interference preventing module 100, the circuit board 110 is exemplified by including a number of soldering holes 110a, as shown in FIG. 1B. Each soldering hole 110a passes through the circuit board 110 from a first surface 111 and an opposite second surface 112 of the circuit board 110. The metal pad 130 is disposed on the first surface 111. Both the first grounding housing 151 and the first surface 111 situates on the same side of the circuit board 110. The first grounding housing 151 includes a first protrusion 151a that is in contact with a part of the metal pad 130.

More specifically, each of the metal pad 130 includes a soldering portion 130a that situates close to and surrounds one soldering hole 110a. A number of fixing lugs 191 of a connector 190 respectively penetrate through the soldering holes 110a from the second surface 112. The fixing lugs 191 are soldered to the soldering portion 130a. Practically, the connector 190 is, for example, an Institute of Electrical and Electronics Engineering (IEEE) 1394 connector, a Universal Serial Bus (USB) connector, or other output/input connectors. Further, the connector 190 is exemplified by soldering to the soldering portion 130a on the first surface 111 via soldering tin.

The metal pad 130 further includes a grounding portion 130b that connects with the soldering portion 130a. The first protrusion 151a of the first grounding housing 151 is in contact with the grounding portion 130b of the metal pad 130. In one embodiment, the area of the grounding portion 130b on the first surface 111 is larger than the area of the soldering portion 130a on the first surface 111. The area of the grounding portion 130b on the first surface 111 is larger than or equal to a cross-section area of the first protrusion 151a on the first surface 111. Therefore the first protrusion 151a can be in well electrical contact with the grounding portion 130b, and thus improving the grounding effect.

The first grounding housing 151 includes a first metal layer 155 for electrically connecting to a ground G. In one embodiment, the first metal layer 155 is electroplated to cover the first grounding housing 151. The first metal layer 155 at least covers the first protrusion 151a of the first grounding housing 151, so the first protrusion 151a electrically contacts with the metal pad 130 through the first metal layer 155. Overall, when the connector 190 undergoes the electromagnetic interference or the electrostatic discharge, the interference or the discharge is guided to the external ground G through the fixing lugs 191, the soldering portion 130a, the grounding portion 130b and the first metal layer 155. As a result, the interference is prevented and the damage caused by electrostatic discharging is avoided.

In one embodiment, the connector 190 is exemplified by including two fixing lugs 191, and the circuit board 110 is exemplified by including two soldering holes 110a, as shown on two sides of the connector 190 in FIG. 1A and FIG. 1B. The metal pad 130 is disposed corresponding to the two soldering holes 110a. Each metal pad 130 includes a soldering portion 130a and a grounding portion 130b. On the other hand, the first protrusion 151a in the present embodiment is exemplified by two cylinders as shown in FIG. 1B. The two cylinders respectively contact with the grounding portion 130b of the metal pad 130 on two sides of the connector 190, so the connector 190 is electrically connected to the external ground G.

The form of the first protrusion 151a, however, is not limited to cylinder. For example, the first protrusion 151a can also be a polygonal pillar, a cone, a polyhedron cone or an arc-shaped protrusion. Any other forms that protruded from the first grounding housing 151 to contact with the metal pad 130 on the first surface 111 are eligible. Further, the number of the soldering holes 110a is equal to the number of the fixing lugs 191 of the connector 190. The shape of the grounding portion 130b on the first surface 111 is corresponding to the shape of the first protrusion 151a. The number of the soldering holes 110a of the circuit board 110 and the disposition of the metal pad 130 are not limited to those as illustrated in FIG. 1A and FIG. 1B.

For instance, when the connector 190 merely has one fixing lug 191, the circuit board 110 has one soldering hole 110a correspondingly. The metal pad 130 is disposed on the circuit board 110 in a manner corresponding to the soldering hole 110a. Accordingly, the first protrusion 151a includes one cylinder that contacts with the grounding portion 130b corresponding to the soldering hole 110a. Similarly, when the connector 190 has four fixing lugs 191, the circuit board 110 has four soldering holes 110a correspondingly. The metal pad 130 is disposed on the circuit board 110 in a manner of corresponding to the four soldering holes 110a. Each of the metal pad 130 corresponding to each soldering hole 110a includes the soldering portion 130a and the grounding portion 130b individually. Furthermore, the first protrusion 151a includes four cylinders that respectively contact with the grounding portion 130b corresponding to the four soldering holes 110a.

Figure 2A:
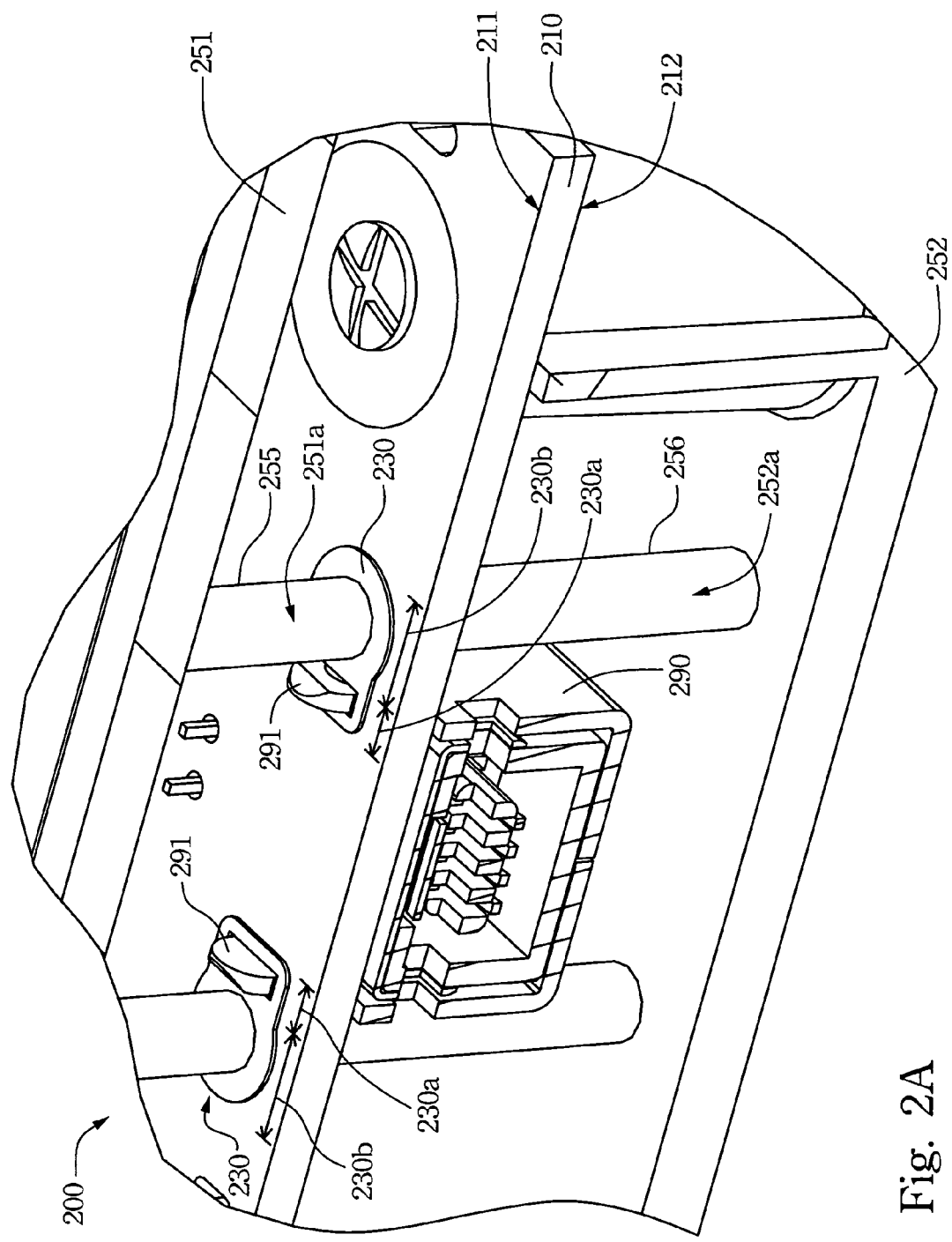
FIG. 2A is a perspective view of an electromagnetic interference preventing module of another embodiment of the invention.
Figure 2B:
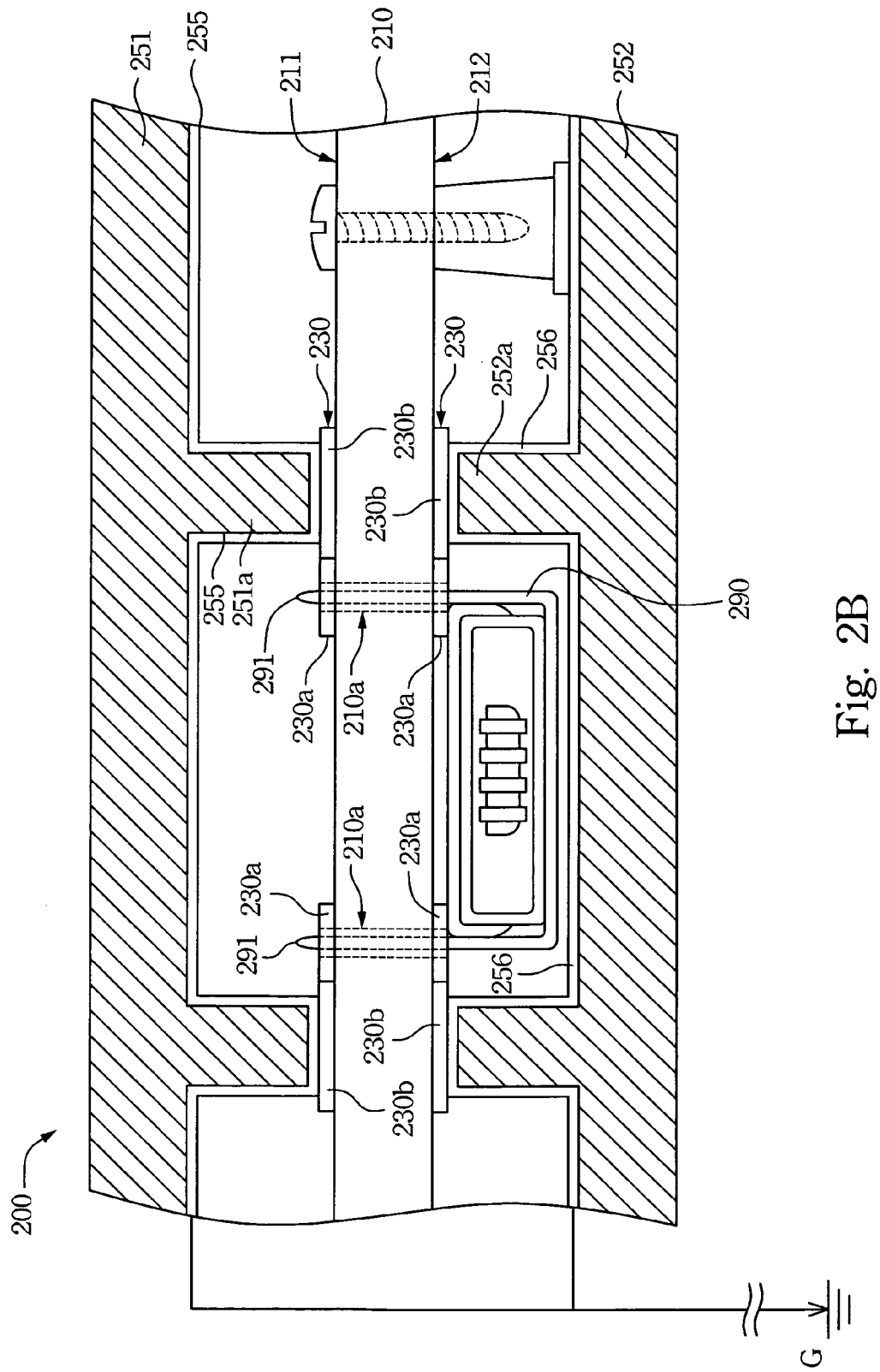
FIG. 2B is a side-view of the electromagnetic interference preventing module in FIG. 2A.

Please refer to FIG. 2A and FIG. 2B at the same time. FIG. 2A is a perspective view of an electromagnetic interference preventing module of another embodiment of the invention. FIG. 2B is a side-view of the electromagnetic interference preventing module in FIG. 2A. In the electromagnetic interference preventing module 200, a circuit board 210 includes several soldering holes 210a. Each soldering hole 210a passes through the circuit board 210 from a first surface 211 to an opposite second surface 212. Metal pads 230 are disposed on both the first surface 211 and the second surface 212. Each of the metal pad 230 on the first surface 211 and the metal pad 230 on the second surface 212 individually includes a soldering portion 230a and a grounding portion 230b. Each fixing lug 291 of the connector 290 penetrates through each soldering hole 210a, and is soldered to the soldering portion 230a on the first surface 211 and the second surface 212.

In the present embodiment, the electromagnetic interference preventing module 200 includes a first grounding housing 251 and a second grounding housing 252 that are disposed on two opposite sides of the circuit board 210 respectively. The first grounding housing 251 is disposed on the first surface 211 and includes a first protrusion 251a, and the second grounding housing 252 is disposed on the second surface 212 and includes a second protrusion 252a. The first protrusion 251a is in contact with the grounding portion 230b on the first surface 211, and the second protrusion 252a is in contact with the grounding portion 230b on the second surface 212.

The area of the grounding portion 230b on the first surface 211 is larger than the area of the soldering portion 230a on the first surface 211. The area of the grounding portion 230b on the second surface 212 is larger than the area of the soldering portion 230a on the second surface 212. Besides that, the area of the grounding portion 230b on the first surface 211 is larger than or equal to a cross-section area of the first protrusion 251a. The area of the grounding portion 230b on the second surface 212 is larger than or equal to a cross-section area of the second protrusion 252a. Therefore, the metal pads 230 are in well contact with the first protrusion 251a and the second protrusion 252a, and the electrical contact quality and the grounding effect are improved.

The first grounding housing 251 includes a first metal layer 255 for electrically connecting to the external ground G. In one embodiment, the first metal layer 255 is electroplated to cover the first grounding housing 251. The first metal layer 255 at least covers the first protrusion 251a. The first protrusion 251a contacts with the grounding portion 230b on the first surface 211 via the first metal layer 255. On the other hand, the second grounding housing 252 includes a second metal layer 256 for electrically connecting to the external ground G. In one embodiment, the second metal layer 256 is electroplated to cover the second grounding housing 252. The second metal layer 256 at least covers the second protrusion 252a. The second protrusion 252a contacts with the grounding portion 230b on the second surface 212 via the second metal layer 256.

Practically, the connector 290 is electrically connected to the external ground G through the fixing lugs 291, the metal pad 230 on the first surface 211 and the first metal layer 255. Besides that, the connector 290 is also electrically connected to the external ground G through a path formed by the fixing lugs 291, the metal pad 230 on the second surface 212 and the second metal layer 256. When the connector 290 undergoes the electromagnetic interference or the electrostatic discharge, the interference or the discharge is guided to the external ground G so that the operating stability of the connector 290 is improved.

In one embodiment, the first protrusion 251a and the second protrusion 252a are respectively exemplified by two cylinders as shown in FIG. 2A. However, the forms of the first protrusion 251a and the second protrusion 252a are not limited thereto. For example, the first protrusion 251a and the second protrusion 252a can individually be one or more polygonal pillars, cones, polyhedron cones or arc-shaped protrusions. In practical use, the shape of the grounding portion 230b on the first surface 211 is corresponding to the shape of the first protrusion 251a, and the shape of the grounding portion 230b on the second surface 212 is corresponding to the shape of the second protrusion 252a. Furthermore, the first protrusion 251a and the second protrusion 252a can be in different forms. For example, the first protrusion 251a includes cylinders while the second protrusion 252a includes polygonal pillars.

Figure 3:
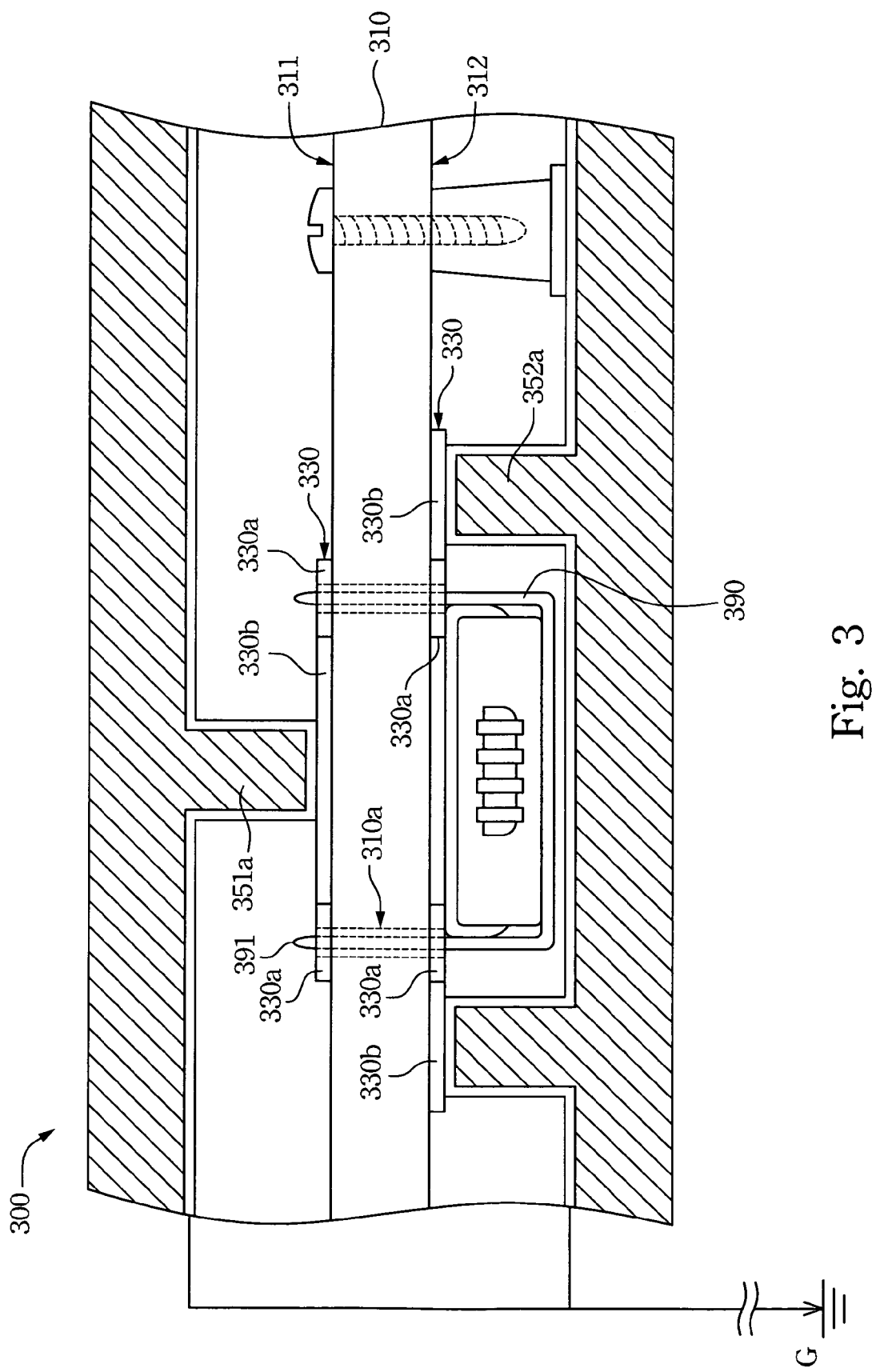
FIG. 3 is a side-view of an electromagnetic interference preventing module of a further embodiment of the invention.

Referring to FIG. 3, a side-view of an electromagnetic interference preventing module of a further embodiment of the invention is illustrated. In the electromagnetic interference preventing module 300, a circuit board 310 includes several soldering holes 310a. Each soldering hole 310a passes through the circuit board 310 from a first surface 311 to an opposite second surface 312. Metal pads 330 are disposed on both the first surface 311 and the second surface 312. Each of the metal pad 330 includes a soldering portion 330a.

In one embodiment, the connector 390 includes two fixing lugs 391, and the circuit board 310 includes two soldering holes 310a on two sides of the connector 390. The soldering portions 330a on the first surface 311 are disposed in a manner corresponding to the two soldering holes 310a on two sides of the connector 390. A grounding portion 330b on the first surface 311 is disposed between the two soldering portions 330a. On the other hand, the soldering portions 330a on the second surface 312 are disposed in a manner corresponding to the two soldering holes 310a on two sides of the connector 390. Two grounding portion 330b on the second surface 312 is disposed on the two sides of the connector 390 as well, and is in contact with the two soldering portions 330a, respectively.

Furthermore, the first protrusion 351a includes a cylinder, and the second protrusion 352a includes two cylinders. The first protrusion 351a contacts with the grounding portion 330b, located between the two parts of the soldering portion 330a, on the first surface 311. The second protrusion 352a contacts with the grounding portion 330b located on the two sides of the connector 390 on the second surface 312. In this manner, the connector 390 is electrically connected to the external ground G through the fixing lugs 391, the metal pad 330 on the first surface 311 and the first protrusion 351a. Also, the connector 390 is electrically connected to the external ground G through the lugs 391, the metal pad 330 on the second surface 312 and the second protrusion 352a.

In one embodiment, the first protrusion 351a and the second protrusion 352a are respectively exemplified by including one cylinder and two cylinders, as shown in FIG. 3. However, the forms of the first protrusion 351a and the second protrusion 352a are not limited to cylinders. For example, the first protrusion 351a and the second protrusion 352a can individually be one or more polygonal pillars, cones, polyhedron cones or arc-shaped protrusions either. In practical use, the shape of the grounding portion 330b on the first surface 311 is corresponding to the first protrusion 351a, and the shape of the grounding portion 330b on the second surface 312 is corresponding to the second protrusion 352a. In another embodiment, the first protrusion 351a and the second protrusion 352a are in different forms. For example, the first protrusion 351a includes one cylinder while the second protrusion 352a includes two polygonal pillars.

In the above-described electromagnetic interference preventing module according to the embodiments of the invention, the protrusion is formed on the grounding housing, and the metal pad is disposed on the circuit board. The fixing lugs of the connector are soldered to the soldering portion of the metal pad. The protrusion is in contact with the grounding portion of the metal pad. As a result, the connector is electrically connected to the external ground to avoid the shortcomings of the electromagnetic interference and the electrostatic discharge, so the operating quality of the connector is improved. Moreover, by utilizing the protrusion to contact with the metal pad, there is no need to add a conductive element between the circuit board and the grounding housing. So the number of the internal elements is decreased and cost is saved.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An electromagnetic interference preventing module comprising:
   a circuit board comprising a first surface, an opposite second surface and at least one soldering hole that passes through the circuit board from the first surface to the second surface;
   a metal pad disposed on the first surface and comprising:
   a soldering portion surrounding the soldering hole; and a grounding portion connecting with the soldering portion;

a connector disposed on the second surface and comprising at least one fixing lug, wherein the fixing lug penetrates through the soldering hole and is soldered to the soldering portion; and a first grounding housing comprising a first protrusion, which is in contact with the grounding portion on the first surface, to electrically connect with the connector.

2. The electromagnetic interference preventing module of claim 1, wherein the first protrusion is a cylinder, a polygonal pillar, a cone, a polyhedron cone or an arc-shaped protrusion.

3. The electromagnetic interference preventing module of claim 1, wherein the shape of the grounding portion on the first surface is corresponding to the shape of the first protrusion.

4. The electromagnetic interference preventing module of claim 1, wherein the area of the grounding portion on the first surface is larger than the area of soldering portion on the first surface.

5. The electromagnetic interference preventing module of claim 1, wherein the area of the grounding portion on the first surface is larger than or equal to a cross-section area of the first protrusion on the first surface.

6. The electromagnetic interference preventing module of claim 1, wherein the metal pad is further disposed on the second surface.

7. The electromagnetic interference preventing module of claim 6, wherein the fixing lug is soldered to the soldering portion on the first surface and on the second surface.

8. The electromagnetic interference preventing module of claim 6, further comprising:

a second grounding housing comprising a second protrusion that is in contact with the grounding portion on the second surface to electrically connect the connector with the second grounding housing.

9. The electromagnetic interference preventing module of claim 8, wherein the second protrusion is a cylinder, a polygonal pillar, a cone, a polyhedron cone or an arc-shaped protrusion.

10. The electromagnetic interference preventing module of claim 9, wherein the shape of the grounding portion on the second surface is corresponding to the shape of the second protrusion.

11. The electromagnetic interference preventing module of claim 1, wherein the first grounding housing comprises:

a first metal layer for electrically connecting to a ground, wherein the first protrusion is covered by the first metal layer and is in contact with the grounding portion on the first surface through the first metal layer.

12. The electromagnetic interference preventing module of claim 11, wherein the first protrusion is a cylinder, a polygonal pillar, a cone, a polyhedron cone or am arc-shaped protrusion.

13. The electromagnetic interference preventing module of claim 12, wherein the area of the grounding portion on the first surface is larger than the area of the soldering portion on the first surface.

14. The electromagnetic interference preventing module of claim 13, wherein the area of the grounding portion on the first surface is larger than or equal to a cross-section area of the first protrusion on the first surface.

15. The electromagnetic interference preventing module of claim 11, wherein the metal pad is further disposed on the second surface.

16. The electromagnetic interference preventing module of claim 15, further comprises:

a second grounding housing comprising a second protrusion that is in contact with the grounding portion on the second surface to electrically connect the connector with the second grounding housing.

17. The electromagnetic interference preventing module of claim 16, wherein the second grounding housing comprises:

a second metal layer for electrically connecting to the external ground, wherein the second protrusion is covered by the second metal layer and is in contact with the grounding portion on the second surface through the second metal layer.

18. The electromagnetic interference preventing module of claim 17, wherein the second protrusion is a cylinder, a polygonal pillar, a cone, a polyhedron cone or an arc-shaped protrusion.

19. The electromagnetic interference preventing module of claim 18, wherein the area of the grounding portion on the second surface is larger than the area of the soldering portion on the second surface.

20. The electromagnetic interference preventing module of claim 19, wherein the area of the grounding portion on the second surface is larger than or equal to a cross-section area of the second protrusion on the second surface.

* * * * *